US010794793B2

(12) United States Patent
Jourdan et al.

(10) Patent No.: US 10,794,793 B2
(45) Date of Patent: Oct. 6, 2020

(54) DEVICE FOR THE DETECTION OF LEAKS AND MODULE FOR THE DETECTION OF LEAKS

(71) Applicant: PFEIFFER VACUUM, Annecy (FR)

(72) Inventors: Pascal Jourdan, Poisy (FR); Laurent Ducimetiere, Annecy (FR)

(73) Assignee: PFEIFFER VACUUM, Annecy (FR)

( * ) Notice: Subject to any disclaimer, the term of this patent is extended or adjusted under 35 U.S.C. 154(b) by 208 days.

(21) Appl. No.: 15/776,633

(22) PCT Filed: Dec. 5, 2016

(86) PCT No.: PCT/EP2016/079769
§ 371 (c)(1),
(2) Date: May 16, 2018

(87) PCT Pub. No.: WO2017/097711
PCT Pub. Date: Jun. 15, 2017

(65) Prior Publication Data
US 2018/0328808 A1 Nov. 15, 2018

(30) Foreign Application Priority Data
Dec. 7, 2015 (FR) ...................................... 15 61927

(51) Int. Cl.
*G01M 3/20* (2006.01)
*G01N 33/00* (2006.01)
(Continued)

(52) U.S. Cl.
CPC ............... *G01M 3/20* (2013.01); *G01N 1/24* (2013.01); *G01N 33/0009* (2013.01); *G06F 3/014* (2013.01); *G01N 2001/2276* (2013.01)

(58) Field of Classification Search
None
See application file for complete search history.

(56) References Cited

U.S. PATENT DOCUMENTS 4,542,291 A * 9/1985 Zimmerman ...... G01D 5/35345
250/231.1
4,988,981 A * 1/1991 Zimmerman ......... A61B 5/1114
345/156

(Continued)

FOREIGN PATENT DOCUMENTS

CN 101223432 A 7/2008
CN 103040168 A 4/2013
(Continued)

OTHER PUBLICATIONS

Combined Chinese Office Action and Search Report dated Oct. 30, 2019 in Chinese Patent Application No. 201680071397.0 (with English translation), 11 pages.
(Continued)

*Primary Examiner* — Paul M. West
*Assistant Examiner* — Mark A Shabman
(74) *Attorney, Agent, or Firm* — Oblon, McClelland, Maier & Neustadt, L.L.P.

(57) ABSTRACT

There is provided a leak detection device configured to check tightness of an object to be tested by a tracer gas, the device including a sniffing probe configured to be connected to a leak detector and/or a spray blower configured to be connected to a source of the tracer gas; and a glove to which the sniffing probe and/or the spray blower is attached. There is also provided a module for detection of leaks, including the device configured to check the checking the tightness of the object to be tested by the tracer gas.

36 Claims, 2 Drawing Sheets

(51) Int. Cl.
  *G06F 3/01* (2006.01)
  *G01N 1/24* (2006.01)
  *G01N 1/22* (2006.01)

(56) References Cited

U.S. PATENT DOCUMENTS

| | | | | |
|---|---|---|---|---|
| 5,445,026 | A * | 8/1995 | Eagan | G01H 3/12 |
| | | | | 73/40.5 A |
| 5,895,871 | A * | 4/1999 | Patton | A61B 5/04005 |
| | | | | 73/866.5 |
| 6,234,021 | B1 * | 5/2001 | Piety | G01H 1/00 |
| | | | | 73/592 |
| 7,051,577 | B2 * | 5/2006 | Komninos | G01M 3/24 |
| | | | | 73/40.5 A |
| 2002/0124631 | A1 * | 9/2002 | Sunshine | G01N 33/0009 |
| | | | | 73/23.2 |
| 2003/0159495 | A1 * | 8/2003 | Cardinale | G01N 1/24 |
| | | | | 73/23.2 |
| 2004/0005715 | A1 * | 1/2004 | Schabron | G01N 27/70 |
| | | | | 436/104 |
| 2004/0194533 | A1 * | 10/2004 | Bohm | G01M 3/205 |
| | | | | 73/23.34 |
| 2008/0314774 | A1 * | 12/2008 | Granadino | G01M 3/226 |
| | | | | 206/216 |
| 2009/0120165 | A1 * | 5/2009 | Lang | G01M 3/205 |
| | | | | 73/40.7 |
| 2010/0308980 | A1 * | 12/2010 | Gosset | H04Q 9/00 |
| | | | | 340/286.02 |
| 2010/0314975 | A1 | 12/2010 | Granadino | |
| 2011/0247399 | A1 | 10/2011 | Schwartz et al. | |
| 2013/0104283 | A1 * | 5/2013 | Ramhorst | B08B 15/026 |
| | | | | 2/160 |
| 2016/0025682 | A1 * | 1/2016 | Walker | G01N 27/9033 |
| | | | | 324/222 |

FOREIGN PATENT DOCUMENTS

| | | |
|---|---|---|
| DE | 28 01 345 A1 | 7/1979 |
| FR | 2 992 723 A1 | 1/2014 |
| FR | 2 992 723 B1 | 10/2015 |
| JP | 2003-18443 A | 1/2003 |
| WO | WO 00/27478 A2 | 5/2000 |

OTHER PUBLICATIONS

International Search Report dated Feb. 28, 2017 in PCT/EP2016/079769 filed Dec. 5, 2016.

* cited by examiner

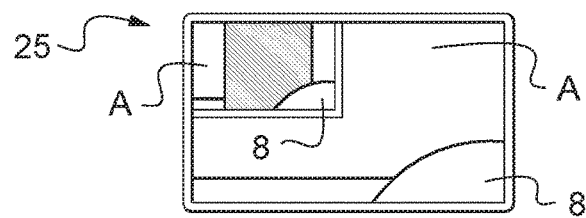
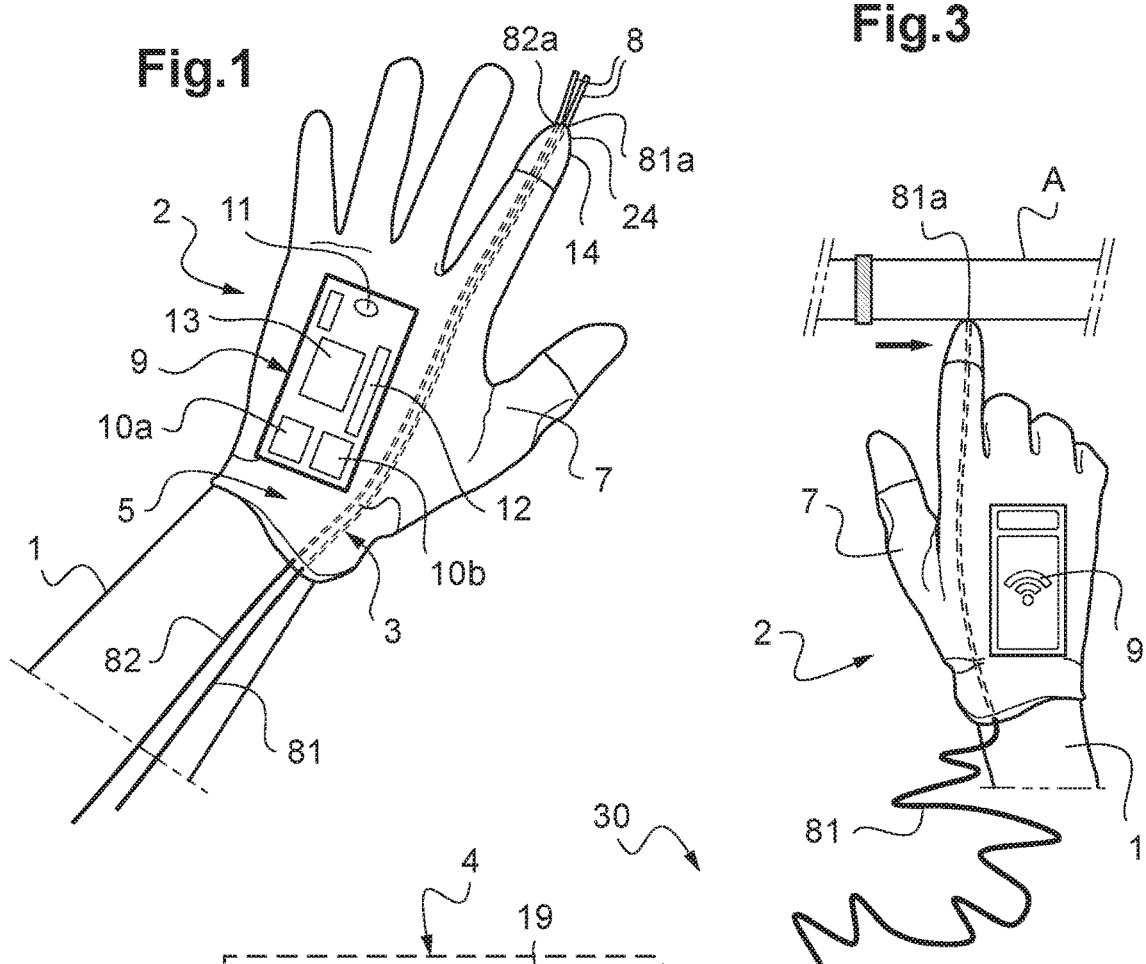
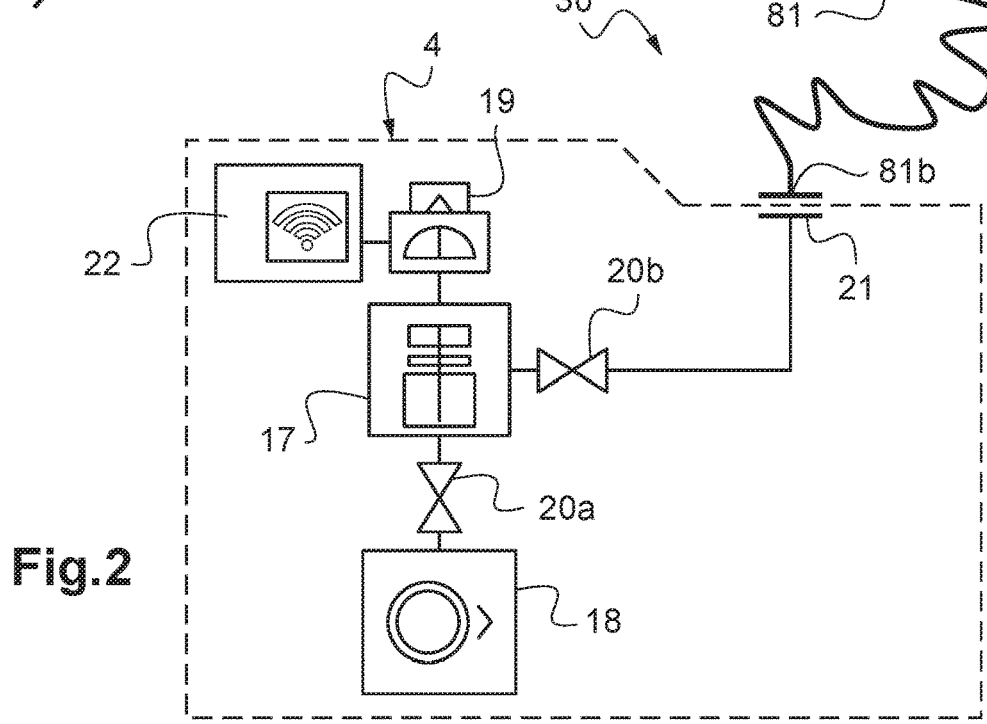

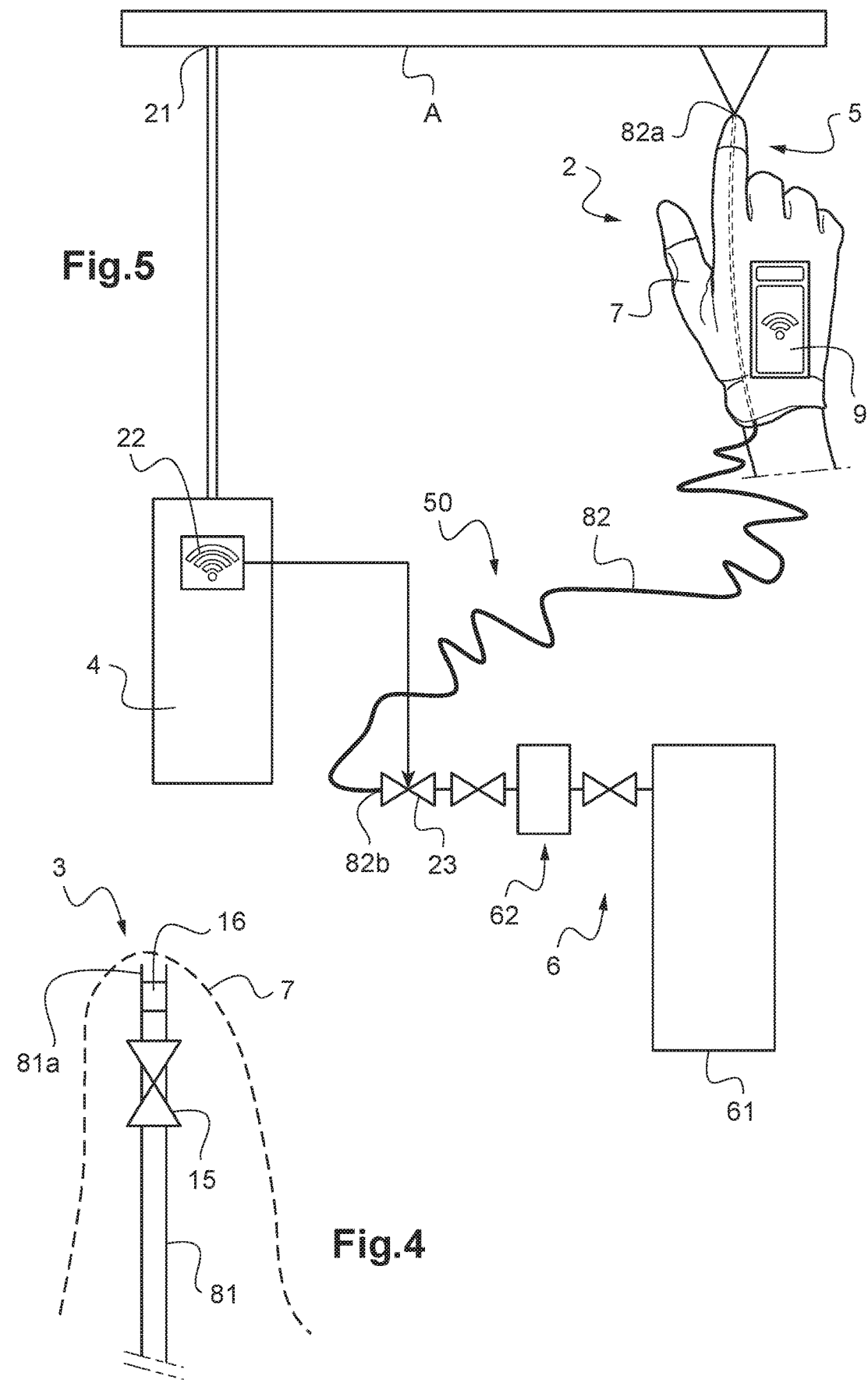

DEVICE FOR THE DETECTION OF LEAKS AND MODULE FOR THE DETECTION OF LEAKS

The present invention concerns a device for the detection of leaks and a module for the detection of leaks comprising said device for checking the tightness of an object to be tested by tracer gas.

A known method for checking the tightness of an object involves performing a test referred to as "sniffing" or "spraying" of tracer gas. This method relies on the detection of the passage of the tracer gas through any leaks in the object to be tested.

In sniffing mode, the possible presence of the tracer gas around an object to be tested filled with the generally pressurized tracer gas is tested with the help of a leak detector connected to a sniffing probe.

In spraying mode, the object to be tested is sprayed with tracer gas using a spray pistol, the interior volume of the object to be tested being connected to a leak detector.

Testing for leaks is carried out by moving the extremity of the sniffing probe or the spray pistol around the object to be tested, in particular at the level of the zones that are likely to show signs of a lack of gastight integrity, for example around gaskets.

Certain zones may be difficult to access, however, in particular when the objects to be tested have complicated and irregular shapes, or in the case of zones to be tested that are not visible to the user, such as dark zones or zones at the rear. These difficulties of access may be accentuated by the generally narrow, long and rigid shape of the extremity of the spray pistol and of the sniffing probe. Manipulation by the user is not an easy task, therefore, in particular when working blind.

Certain installations to be tested additionally exhibit large dimensions, which may complicate testing for leaks. In fact, the space taken up by the installation may oblige the user to adopt unstable postures, forcing him to make use of the structure of the installation in order to reach any zones that are difficult to access. The user's hands may then be occupied in order to allow him to continue. However, the user may need to have his hands free for the manipulation of tools, for example in order to remove a protective cover or in order to illuminate the testing zone. Similarly, in the course of testing, the user may find that the is remote from the leak detector and may experience the need to manipulate a remote control permitting him to operate a leak detector remotely.

Furthermore, the manipulation of the spray pistol or of the sniffing probe may cause pain in the hands of an operator who is responsible for testing the tightness of objects on a repeated, continual and daily basis.

One of the aims of the present invention is thus to propose a leak detection device and a detection module which address the aforementioned disadvantages, at least in part, in particular by proposing a leak detection device that is more ergonomic and easier to manipulate.

For this purpose, the invention has as its object a device for the detection of leaks that is configured to check the tightness of an object to be tested by tracer gas, said leak detection device comprising a sniffing probe intended to be connected to a leak detector and/or a spray blower intended to be connected to a source of tracer gas, characterized in that it includes a glove to which the sniffing probe and/or the spray blower is attached.

The sniffing probe and/or the spray blower carried by the glove thus permits the user to perform a more intuitive and more ergonomic manipulation. He is thus able to gain easier access to the less visible zones of the object to be tested, such as rear zones or dark zones, with the dexterity that the agility of his hand provides and with a spatial awareness facilitated by manual contact with the object to be tested. In addition, the carrying of the sniffing probe and/or of the spray blower by the glove no longer immobilizes the user's hand, who may use it for other purposes. Pains in the hands associated with the prolonged use of the sniffers/pistols of the prior art are avoided in addition.

According to one or a plurality of characterizing features of the leak detection device, considered alone or in combination:

- the sniffing probe and/or the spray blower includes a line for the circulation of the gases comprising a first orifice for the inlet or the outlet of the gases and a second orifice intended to be connected to a leak detector or to a source of tracer gas,
- the gas circulation line is flexible,
- the gas circulation line passes through the glove by being integrated into the glove,
- the gas circulation line extends along a part of the glove intended to cover a finger of the user, in particular the index finger, and leads to the level of the extremity of said part of the glove corresponding to the tip of the finger,
- the leak detection device includes a control device carried by the glove and configured to communicate with a control unit of the leak detector,
- the control device includes at least one means of activation configured to control the initiation of a measurement of the concentration of tracer gas and/or of a reinitialization of the background noise of the leak detector,
- the leak detection device includes a display device carried by the glove, configured to display a measurement signal from the leak detector and/or in order to provide information in respect of the state of the leak detector,
- the display device includes a screen configured to display any change in the concentration of tracer gas over time measured by the leak detector,
- the control device and/or the display device include means of wireless communication in order to communicate with a control unit of the leak detector,
- the leak detection device includes an illumination device carried by the glove,
- the leak detection device includes a camera carried by the glove and a remote visualization system configured to display the images taken by the camera,
- the remote visualization system is also configured to display images taken earlier by the camera,
- the leak detection device includes a predefined conductance arranged between the first and the second orifice of the gas circulation line of the sniffing probe, the predefined conductance being configured to limit the flow of gas intended to be drawn in via a pumping device of the leak detector,
- the leak detection device includes at least one filter arranged between the first and the second orifice of the gas circulation line of the sniffing probe,
- the control device carried by the glove includes a means of activation configured to operate the opening of a valve permitting the passage of a flow of tracer gas in the gas circulation line of the spray blower.

The invention also has as its object a module for the detection of leaks comprising a leak detector and/or a source of tracer gas, characterized in that it includes a leak detection device as described previously.

According to one or a plurality of characterizing features of the module for the detection of leaks, taken alone or in combination:

the leak detector includes a control unit configured to communicate with a control device carried by the glove of the leak detection device, the module for the detection of leaks includes a valve permitting the passage of a flow of tracer gas in the gas circulation line of the spray blower, the opening of the valve being capable of operation via a means of activation of the control device carried by the glove.

Other characterizing features and advantages of the invention will be appreciated from the following description, which is given by way of example, and without limitation, with respect to the accompanying drawings, in which:

FIG. 1 depicts a schematic view of the hand of a user carrying a leak detection device, FIG. 2 depicts a schematic view of an example of a leak detection device connected to a leak detector in order to test the tightness of an object to be tested in sniffing mode, FIG. 3 depicts an example of the display of a remote visualization system, FIG. 4 depicts a schematic view of a detail of the leak detection device in FIG. 2, and FIG. 5 depicts a schematic view of an example of the leak detection device connected to a source of tracer gas in order to test the tightness of an object to be tested in spraying mode.

In these figures, the identical elements bear the same reference numbers. The following embodiments are examples. Although the description relates to one or a plurality of embodiments, this does not necessarily signify that each reference concerns the same mode of implementation, or that the characterizing features apply only to a single mode of implementation. Simple characterizing features of different modes of implementation may also be combined in order to provide other embodiments.

In the rest of the description, the terms "upstream" and "downstream" are used with reference to the direction of flow of the gases.

FIG. 1 depicts a schematic view of a hand of a user 1 carrying a leak detection device 2 configured to check the tightness of an object to be tested by tracer gas.

The leak detection device 2 comprises a sniffing probe 3 intended to be connected to a leak detector 4 (FIG. 2) and/or a spray blower 5 intended to be connected to a source of tracer gas 6 (FIG. 5).

In the example in FIG. 1, the leak detection device 2 comprises a sniffing probe 3 and a spray blower 5, the user being able to choose the use of one or the other in order to test an object either in sniffing mode, or in spraying mode. The leak detection device 2 may also include only a sniffing probe 3 (FIG. 2) or only a spray blower 5 (FIG. 5).

Helium or hydrogen are generally used as a tracer gas because these gases pass through small leaks more readily than the other gases, due to the small size of their molecule and their high speed of displacement.

The leak detection device 2 also includes a glove 7 to which the sniffing probe 3 and/or the spray blower 5 is attached (FIG. 1).

The glove 7 may be made of a textile material, such as a woven fabric, and/or of an elastic material. It adopts the form of the hand of the user 1, preferably covering the fingers and possibly the wrist in order to ensure an improved grip.

The sniffing probe 3 and/or the spray blower 5 includes at least one gas circulation line 81, 82 comprising a first orifice 81a, 82a for the inlet or the outlet of gas and a second orifice 81b, 82b intended to be connected to a leak detector 4 or to a source of tracer gas 6.

The gas circulation line 81, 82 passes through the glove 7 by being integrated into the glove 7 in order to be protected from the external environment and in order to avoid becoming caught during movements by the user. It is stitched or thermally bonded, for example, to the textile material of the glove 7 between two strips of woven fabric.

The gas circulation line 81, 82 exits from the glove 7, for example at the level of the wrist, in order to be connected to the leak detector 4 and/or to the source of tracer gas 6 via one or a plurality of tube elements. On the exterior of the glove 7, the gas circulation line 81, 82 may thus possess a length of several metres.

At the level of the glove 7, the gas circulation line 81, 82 extends along the back of the hand, for example, as well as along a part 7a of the glove 7 covering a finger of the user 1, such as along the index finger. The gas circulation line 81, 82 leads, for example, from the glove 7 at the level of the extremity of said part of the glove 7 corresponding to the tip of the finger of the user 1 (FIGS. 1, 2, 4 and 5). In particular, a gas circulation line 81, 82 integrated into the dorsal part of the glove 7 makes it possible to limit the risks of deformation of the latter by closing the fist.

It is proposed in addition that the gas circulation line 81, 82 is flexible, in order to permit the movements of the fingers of the hand. The line 81, 82 is made of a plastic material, for example.

The leak detection device 2 may also include a small replaceable tip 8, for example having a rigid tubular form, cooperating with a complementary means carried by the glove 7, for example by screwing. The complementary means may be arranged at the tip of the part of the glove 7 covering the finger of the user 1. It is thus possible to extend the gas circulation line 81, 82 at the level of the first orifice 81a, 82a in order to facilitate access by the sniffing probe 3 and/or by the spray blower 5 into testing zones of small dimensions which are less than the dimensions of the finger.

The sniffing probe 3 and/or the spray blower 5 carried by the glove 7 thus permits the user 1 to perform a more intuitive and more ergonomic manipulation. He is thus able to gain easier access to the less visible zones of the object to be tested, such as rear zones or dark zones, with the dexterity that the agility of his hand provides and with a spatial awareness facilitated by manual contact with the object to be tested. Moreover, the carrying of the sniffing probe 3 and/or of the spray blower 5 by the glove 7 no longer immobilizes the hand of the user, who is able to use it for other purposes. Pains in the hands associated with the prolonged use of the sniffers/pistols of the prior art are avoided in addition.

The leak detection device 2 may also include a control device 9 configured to communicate with a control unit 22 of the leak detector 4.

The control device 9 is attached, for example, to the part of the glove 7 intended to cover the back of the hand.

The control device 9 may include at least one means of activation 10a, 10b configured to check at least one parameter of the leak detector 4 such as a measurement of the concentration of tracer gas that is representative of the rate of leakage of the object to be tested A and/or in order to control the reinitialization of the background noise.

The measurement of the concentration of tracer gas is performed by means of a gas analyser of the leak detector 4, which analyses the gases collected by a pumping device of the detector 4.

The reinitialization of the background noise permits a nil value to be attributed to a measurement of the concentration of tracer gas. This makes it possible to reveal the presence of a leak more easily when the level of the background noise is high without waiting for a drop in the level of tracer gas and without ventilating the atmosphere.

The means of activation includes, for example, a touch pad 10a, 10b comprising a resistive or capacitive sensor, configured to detect the pressure of a finger of the user 1. Thus, a press on a first touch pad 10a makes it possible to control a measurement of the concentration of tracer gas by the leak detector 4, and a press on a second touch pad 10b makes it possible to control the reinitialization of the background noise.

The functions of the remote control for the leak detector 4 may thus be arranged at the level of the glove 7, which relieves the user 1 of the need to carry a remote control and avoids the immobilisation of his hand. Furthermore, the activation of the control device 9 by the other hand is easy.

Other means of activation of the control device 9 may be proposed.

For example, the means of activation may include a motion sensor carried by the glove 7, configured to detect a movement of a finger of the hand of the user 1 wearing the glove 7. According to another example, the means of activation may include strain gauges arranged on two parts of the glove 7 covering the fingers of the user 1 in order to detect any contact between two parts of the glove 7. In this way, the movements of the fingers may be sufficient for the user 1 to control a parameter of the leak detector 4, such as a measurement of the concentration of tracer gas or a reinitialization of the background noise.

The control device 9 may also include means of activation configured in order to control other parameters of the leak detector 4, such as the regulation of the noise level that is representative of the rate of leakage measured by the leak detector 4. In fact, the leak detector 4 or the leak detection device 2 may include a noise-emitting device, such as a beeper or a loudspeaker, of which the frequency increases with the increase in the measurement signal that is representative of the rate of leakage. The regulation of the noise level of the noise-emitting device, either remotely in the leak detector 4 or integrated in the glove 7, may permit the user 1, remotely from the leak detector 4 or in a noisy environment, to increase the noise of the noise-emitting device without moving.

The leak detection device 2 may also include a display device carried by the glove 7, configured to display a measurement signal from the leak detector 4 and/or in order to provide information in respect of the state of the leak detector 4.

The display device communicates with the control unit 22 of the leak detector 4 in order to recover the measurement data from the gas analyser of the detector 4.

The display device is attached, for example, to a part of the glove 7 intended to cover the back of the hand, for example to one side of the control device 9.

The display device may include a first visual indicator 11, such as a two-colour indicator, in order to provide information in respect of the state of the detector, namely if the leak detector 4 is in the process of performing a measurement. The information in respect of the state of the leak detector 4 permits the user, for example, who is not able to visualize the leak detector 4 directly, to satisfy himself that he is actually in the process of taking a measurement in order to determine the absence of leaks in the presence of a weak or nil measurement signal.

The display device may include a second visual indicator 12 in order to display a measurement signal for the concentration of tracer gas transmitted by the leak detector 4.

The second visual indicator 12 is a screen or a bar graph, for example, displaying in the form of graphic bars indicating the intensity, or in numerical form, or expressed as a percentage, or in the form of individual pictograms, information in respect of the intensity of the concentration of tracer gas that is representative of the rate of leakage of the object to be tested for one or a plurality of decades.

The second visual indicator 12 may also be configured to change colour when the measurement signal crosses at least one detection threshold.

The display device may include a screen 13 configured to display any change over time in the measurement signal for the concentration of tracer gas. This may permit the user 1 to compare a plurality of peaks in the measurement signal with each other and thus, for example, to determine more easily the location of the leak exhibiting the highest rate of leakage.

It is also possible to propose that the display device and the means of activation 10a, 10b of the control device 9 are formed by one and the same interface, such as a touch screen.

The leak detection device 2 may in addition include a vibratory actuator carried by the glove 7 arranged at the level of the touch screen, for example, in order to cause the glove 7 to vibrate, for example when the leak detector 4 initiates a measurement or when the measurement signal crosses at least one detection threshold.

The control device 9 and/or the display device 11, 12, 13 may include means of wireless communication in order to communicate with a control unit 22 of the leak detector 4. The means of wireless communication are of the WIFI, Bluetooth or some other type, for example. Potentially inconvenient wired connections between the leak detection device 2 and the user 1 are limited in this way.

The leak detection device 2 may also include an illumination device 14 carried by the glove 7, comprising a light source such as an electroluminescent diode (DEL, or LED for "Light-Emitting Diode" in English), a switch in order to turn on/turn off the light source and a power supply battery for the light source or a power supply cable to a remote power supply source.

The light source of the illumination device 14 is arranged, for example, at the level of the extremity of the part of the glove 7 covering the finger of the user 1, that is to say at the tip of the finger and in proximity to the first orifice 81a of the gas circulation line 81. The testing zone around the object to be tested may thus be illuminated easily and with precision without the hand of the user 1 being immobilized for the manipulation of a pocket lamp.

It is also possible to provide a colour code for the illumination light produced by the illumination device 14, defined depending on the crossing by the measurement signal of one or a plurality of detection thresholds. The user 1 may thus easily and rapidly visualize the measured rate of leakage without having to free a hand in order to pick up a remote control.

The leak detection device 2 may also include a camera 24 carried by the glove 7, for example integrated with or attached to the glove 7 at the tip of the index finger, next to the orifices 81*a*, 82*a*, and a remote visualization system 25 configured to display the images taken by the camera 24 (FIG. 3).

The camera 24 makes it possible to facilitate visualisation by the user during the detection of leaks in poorly accessible zones where no direct view is possible. The video images are displayed on the remote visualization system 25 that is directly visible by the user, such as a screen that is remote in relation to the glove 7 and the leak detector 4, or such as augmented reality glasses.

The images are transmitted, for example, by default in real time and make it possible to visualize the location of the glove 7, that is to say orifices 81*a*, 82*a* in relation to the object to be tested A.

The remote visualization system 25 may also be configured to display images taken earlier by the camera 24. This additional display may be located, for example, in a corner of the screen of the remote visualization system 25, in addition displaying the images transmitted in real time (FIG. 3).

In fact, in the case of a leak detected in sniffing mode, a delay may occur between the moment at which a gaseous mixture escaping from the leak is drawn in and the moment of the detection per se by the leak detector 4. Location of the leak when the glove 7 moves is facilitated by displaying the images taken earlier; this prevents the glove 7 from having moved for a certain distance at the moment of the detection of the leak, with the result that the image seen by the user no longer corresponds to the precise location of the leak.

The images taken earlier may be displayed with a predetermined time lag. These earlier images may run continuously or may be replaced, for example, on the order of the control unit 22, when the concentration of tracer gas exceeds a predetermined threshold or a previous level of concentration of tracer gas.

Image processing makes it possible, for a given sniffing probe 3 (given conductance), to display the image taken by the camera 24 with a predetermined time lag, corresponding to the "real" position of the leak. This delay is determined by the predefined conductance 15 of the line for the circulation of the gases 81 of the sniffing probe 3. Typically, and depending on the geometry of the line for the circulation of the gases 81, this delay may extend from a few tenths of a second to a few tens of seconds. At the same time, it is perfectly defined for a given line geometry.

The images taken earlier displayed on the remote visualization system 25 may also correspond to frozen images taken for peak concentrations of tracer gas on the order of the control unit 22. The images may be renewed, for example, when the concentration of tracer gas exceeds a predetermined threshold or exceeds a preceding level of tracer gas concentration.

FIGS. 2 and 4 depict more specifically an illustrative embodiment of a module for the detection of leaks 30 comprising a leak detector 4 and a leak detection device 2 connected to the leak detector 4 via a gas circulation line 81.

As may be seen more clearly in FIG. 4, the leak detection device 2 includes a predefined conductance 15 arranged between the first and the second orifice 81*a*, 81*b* of the gas circulation line 81 of the sniffing probe 3. The predefined conductance 15 is configured to limit the flow of gas drawn in via the pumping device of the leak detector 4. The predefined conductance 15 is provided, for example, by a capillary tube, a nozzle such as a pierced ruby, or a porous membrane or a needle.

The leak detection device 2 also includes at least one filter 16 mounted in the gas circulation line 81 in series with the predefined conductance 15, for example upstream of the latter.

The filter 16 filters any dust that may originate from the external atmosphere, thereby permitting the gas circulation line 81 to be prevented from becoming clogged. A plurality of filters can be provided in series, upstream of the predefined conductance 15, such as a first filter made of sintered metal for the dust comprised between 10 and 20 µm and a second, felt fibre-based filter for the finer dust, for example comprised between 5 and 10 µm.

It is proposed in addition to position the filter 16 as closely as possible to the first orifice 81*a* of the line 81 in such a way as to prevent the pollution of the line 81.

The predefined conductance 15 may be arranged in the portion of the gas circulation line 81 which is integrated into the glove 7 or may be remote from the filter 16, for example by being arranged at the level of the arm of the user.

Returning to FIG. 2, it will be appreciated that the leak detector 4 includes a gas analyser 19, such as a mass spectrometer, and a pumping device.

According to one illustrative embodiment, the leak detector 4 includes a control unit 22, such as a microcontroller or a computer, configured to communicate with the control device 9 carried by the glove 7.

The control unit 22 is configured to initiate a measurement of the concentration of tracer gas by the gas analyser 19 and/or in order to control the reinitialization of the background noise, upon receiving a signal transmitted by the control device 9 of the leak detection device 2.

The pumping device includes, for example, a secondary pump 17, such as a turbomolecular pump, and a primary pump 18 mounted in series. The primary pump 18 is a membrane pump, for example, which draws in the gases and discharges them at atmospheric pressure having pumping speeds in the order of 0.25 m$^3$/h to 4.3 m$^3$/h. The gas analyser 19 is connected to the suction side of the secondary pump 17, of which the discharge is connected to the suction side of the primary pump 18 via a first isolation valve 20*a*. The inlet 21 of the leak detector 4, arranged upstream of the pumping device via a second isolation valve 20*b*, is connected to the second orifice 81*b* of the gas circulation line 81 of the leak detection device 2, either directly or by means of intermediate flexible tubes.

In operation, the object to be tested A is filled with tracer gas, generally pressurized, and the possible presence of the tracer gas is tested by moving the finger around the object to be tested A. The sniffing probe 3 connected to the leak detector 4 and carried by the glove 7 draws in the surrounding gases via the first orifice 81*a*. One part of the gases collected in this way, possibly containing the tracer gas that is indicative of a leak, is then analysed by the gas analyser 19, which provides a measurement signal for the concentration of tracer gas.

FIG. 5 depicts an illustrative embodiment of a leak detection device 2 connected to a source of tracer gas 6 by a gas circulation line 82.

The source of tracer gas 6 includes, for example, a pressurized cylinder of tracer gas 61 and a pressure regulator 62 connected to the cylinder of tracer gas 61.

The module for the detection of leaks 50 in addition includes a valve 23, such as a solenoid valve, permitting the passage of a flow of tracer gas in the gas circulation line 82 of the spray blower 5. The valve 23 is arranged, for example, at the outlet of the source of tracer gas 6, interposed between the outlet of the pressure regulator 62 and the second orifice 82b of the gas circulation line 82 of the spray blower 5.

The opening of the valve 23 may be operated by a means of activation of the control device 9 carried by the glove 7.

The operation of opening the valve 23 may thus be performed by wireless communication means, by activation means arranged on the glove 7, for example of the tactile sensor type such as a touch screen, a touch pad or strain gauges or such as a motion sensor. In this way, the movements of the fingers may be sufficient for the user 1 to control the initiation of the blow spraying of tracer gas by the spray blower 5.

The source of gas 6 and the leak detector 4 may in addition be carried by a common frame, in order to facilitate the displacement of the detection module 30, 50 and to facilitate the connection of the valve 23 to the control unit 22 of the leak detector 4.

In operation, the object to be tested A is connected to a leak detector 4, for example such as that described in the example in FIG. 2, and possibly to an auxiliary pumping device (not represented here).

Testing for the possible presence of the tracer gas involves moving the finger, and thus the first orifice 82a of the spray blower 5, around the object to be tested A in order to spray it with tracer gas. The inlet 21 of the leak detector 4 collects a part of the gases contained in the object to be tested A. A part of the gases collected in this way, potentially containing the tracer gas that is indicative of a leak, is then analysed by the gas analyser 19, which provides a measurement signal for the concentration of tracer gas.

The invention claimed is:

1. A device for detection of leaks and being configured to check tightness of an object to be tested by a tracer gas, the device comprising:
    a sniffing probe configured to be connected to a leak detector;
    a glove to which the sniffing probe is attached,
    wherein the sniffing probe includes a line for circulation of gases and comprises a first orifice for an inlet or an outlet of the gases and a second orifice configured to be connected to the leak detector; and
    a predefined conductance arranged between the first and the second orifices of the line for circulation of gases of the sniffing probe, the predefined conductance being configured to limit a flow of gas configured to be drawn in via a pumping device of the leak detector.

2. The device for the detection of leaks according to claim 1, wherein the line for circulation of gases is flexible.

3. The device for the detection of leaks according to claim 1, wherein the line for circulation of gases passes through the glove by being integrated into the glove.

4. The device for the detection of leaks according to claim 1, wherein the line for circulation of gases extends along a part of the glove and is configured to cover a finger of a user, and leads to a level of an extremity of the part of the glove corresponding to a tip of the finger.

5. The device for the detection of leaks according to claim 1, further comprising a control device carried by the glove and being configured to communicate with a control unit of the leak detector.

6. The device for the detection of leaks according to claim 5, wherein the control device includes at least one means of activation configured to control an initiation of a measurement of a concentration of the tracer gas and/or of a reinitialization of a background noise of the leak detector.

7. The device for the detection of leaks according to claim 5 wherein the control device includes means of wireless communication to communicate with the control unit of the leak detector.

8. The device for the detection of leaks according to claim 5, wherein the control device carried by the glove includes a means of activation configured to operate an opening of a valve permitting passage of a flow of the tracer gas in the line for circulation of gases of the spray blower.

9. The device for the detection of leaks according to claim 1, further comprising a display device carried by the glove and being configured to display a measurement signal from the leak detector and/or to provide information of a state of the leak detector.

10. The device for the detection of leaks according to claim 9, wherein the display device includes a screen configured to display any change in a concentration of the tracer gas over time measured by the leak detector.

11. The device for the detection of leaks according to claim 9, wherein the display device includes means of wireless communication to communicate with a control unit of the leak detector.

12. The device for the detection of leaks according to claim 1, further comprising an illumination device carried by the glove.

13. The device for the detection of leaks according to claim 1, further comprising a camera carried by the glove and a remote visualization system configured to display images taken by the camera.

14. The device for the detection of leaks according to claim 13, wherein the remote visualization system is further configured to display images taken earlier by the camera.

15. The device for the detection of leaks according to claim 1, further comprising at least one filter arranged between the first and the second orifices of the line for circulation of gases.

16. A module for detection of leaks comprising:
    a leak detector and/or a source of tracer gas; and
    a leak detection device according to claim 1.

17. The module for detection of leaks according to claim 16, wherein the leak detector includes a control unit configured to communicate with a control device carried by the glove of the leak detection device.

18. The module for detection of leaks according to claim 16, further comprising a valve permitting passage of a flow of the tracer gas in the line for circulation of gases of a spray blower, an opening of the valve being configured to operate via a means of activation of a control device carried by the glove.

19. A device for detection of leaks and being configured to check tightness of an object to be tested by a tracer gas, the device comprising:
    a spray blower configured to be connected to a source of the tracer gas;
    a glove to which the spray blower is attached,
    wherein the spray blower includes a line for circulation of gases and comprises a first orifice for an inlet or an outlet of the gases and a second orifice configured to be connected to the source of the tracer gas.

20. The device for the detection of leaks according to claim 19, wherein the line for circulation of gases is flexible.

21. The device for the detection of leaks according to claim 19, wherein the line for circulation of gases passes through the glove by being integrated into the glove.

22. The device for the detection of leaks according to claim 19, wherein the line for circulation of gases extends along a part of the glove and is configured to cover a finger of a user, and leads to a level of an extremity of the pan of the glove corresponding to a tip of the finger.

23. The device for the detection of leaks according to claim 19, further comprising a control device carried by the glove and being configured to communicate with a control unit of the device for detection of leaks.

24. The device for the detection of leaks according to claim 23, wherein the control device includes at least one means of activation configured to control an initiation of a measurement of a concentration of the tracer gas and/or of a reinitialization of a background noise of the device for detection of leaks.

25. The device for the detection of leaks according to claim 23, wherein the control device includes means of wireless communication to communicate with the control unit of the device for detection of leaks.

26. The device for the detection of leaks according to claim 23,
wherein the control device carried by the glove includes a means of activation configured to operate an opening of a valve permitting passage of a flow of the tracer gas in the line for circulation of gases of the spray blower.

27. The device for the detection of leaks according to claim 19, further comprising a display device carried by the glove and being configured to display a measurement signal from the leak detector and/or to provide information of a state of the device for detection of leaks.

28. The device for the detection of leaks according to claim 21, wherein the display device includes a screen configured to display any change in a concentration of the tracer gas over time measured by the device for detection of leaks.

29. The device for the detection of leaks according to claim 27, wherein the display device includes means of wireless communication to communicate with the control unit of the device for detection of leaks.

30. The device for the detection of leaks according to claim 19, further comprising an illumination device carried by the glove.

31. The device for the detection of leaks according to claim 19, further comprising a camera carried by the glove and a remote visualization systema configured to display images taken by the camera.

32. The device for the detection of leaks according to claim 31, wherein the remote visualization system is further configured to display images taken earlier by the camera.

33. The device for the detection of leaks according to claim 19, further comprising at least one filter arranged between the first and the second orifices of the line for circulation of gases.

34. A module for detection of leaks comprising:
a leak detector and/or a source of tracer gas; and
a leak detection device according to claim 19.

35. The module for detection of leaks according to claim 34, wherein the leak detector includes a control unit configured to communicate with a control device carried by the glove of the leak detection device.

36. The module for detection of leaks according to claim 34,
further comprising a valve permitting passage of a flow of the tracer gas in the line for circulation of gases of the spray blower, an opening of the valve being configured to operate via a means of activation of a control device carried by the glove.

* * * * *